(12) United States Patent
Kotter

(10) Patent No.: US 9,494,464 B2
(45) Date of Patent: Nov. 15, 2016

(54) TERAHERTZ IMAGING DEVICES AND SYSTEMS, AND RELATED METHODS, FOR DETECTION OF MATERIALS

(71) Applicant: BATTELLE ENERGY ALLIANCE, LLC, Idaho Falls, ID (US)

(72) Inventor: Dale K. Kotter, Shelley, ID (US)

(73) Assignee: Battelle Energy Alliance, LLC, Idaho Falls, ID (US)

(*) Notice: Subject to any disclaimer, the term of this patent is extended or adjusted under 35 U.S.C. 154(b) by 133 days.

(21) Appl. No.: 13/771,871

(22) Filed: Feb. 20, 2013

(65) Prior Publication Data

US 2014/0231648 A1 Aug. 21, 2014

(51) Int. Cl.
| | | |
|---|---|---|
| *G01J 1/42* | (2006.01) | |
| *G01J 3/42* | (2006.01) | |
| *H01Q 9/27* | (2006.01) | |
| *H01Q 21/06* | (2006.01) | |
| *G01J 5/02* | (2006.01) | |
| *G01J 5/08* | (2006.01) | |
| *G01V 8/00* | (2006.01) | |
| *G01N 21/3581* | (2014.01) | |

(52) U.S. Cl.
CPC .................. *G01J 3/42* (2013.01); *G01J 5/023* (2013.01); *G01J 5/0837* (2013.01); *G01N 21/3581* (2013.01); *G01V 8/005* (2013.01); *H01Q 9/27* (2013.01); *H01Q 21/062* (2013.01)

(58) Field of Classification Search
CPC ... G01N 21/3581; H01Q 21/062; H01Q 9/27
USPC ...................................................... 250/208.2
See application file for complete search history.

(56) References Cited

U.S. PATENT DOCUMENTS

| | | |
|---|---|---|
| 2,498,461 A | 2/1950 | Skellett |
| 4,533,829 A | 8/1985 | Miceli et al. |
| 5,450,053 A | 9/1995 | Wood |

(Continued)

FOREIGN PATENT DOCUMENTS

| | | |
|---|---|---|
| WO | 2007070541 A3 | 4/2009 |
| WO | 2012153210 A2 | 11/2012 |

OTHER PUBLICATIONS

"Gangbuster frequency selective surface metamaterials in terahertz band", Electronics Letters Oct. 23, 2008, vol. 44, No. 22, pp. 1-2, to Shelton et al.*

(Continued)

*Primary Examiner* — David J Makiya
*Assistant Examiner* — Kenneth J Malkowski
(74) *Attorney, Agent, or Firm* — TraskBritt

(57) ABSTRACT

Terahertz imaging devices may comprise a focal plane array including a substrate and a plurality of resonance elements. The plurality of resonance elements may comprise a conductive material coupled to the substrate. Each resonance element of the plurality of resonance elements may be configured to resonate and produce an output signal responsive to incident radiation having a frequency between about a 0.1 THz and 4 THz range. A method of detecting a hazardous material may comprise receiving incident radiation by a focal plane array having a plurality of discrete pixels including a resonance element configured to absorb the incident radiation at a resonant frequency in the THz, generating an output signal from each of the discrete pixels, and determining a presence of a hazardous material by interpreting spectral information from the output signal.

23 Claims, 5 Drawing Sheets

(56) References Cited

U.S. PATENT DOCUMENTS

| | | | |
|---|---|---|---|
| 6,617,963 | B1 | 9/2003 | Watters et al. |
| 7,095,027 | B1 * | 8/2006 | Boreman ................. G01J 5/08 250/332 |
| 7,436,373 | B1 * | 10/2008 | Lopes et al. ................. 343/909 |
| 7,652,572 | B2 | 1/2010 | Roybal et al. |
| 7,792,644 | B2 | 9/2010 | Kotter et al. |
| 8,071,931 | B2 | 12/2011 | Novack et al. |
| 8,901,507 | B2 | 12/2014 | Kotter |
| 2006/0111619 | A1 * | 5/2006 | Castiglione et al. ......... 600/300 |
| 2006/0210279 | A1 | 9/2006 | Hillis et al. |
| 2008/0060455 | A1 | 3/2008 | Coyle |
| 2008/0156991 | A1 * | 7/2008 | Hu et al. .................... 250/341.1 |
| 2009/0125254 | A1 | 5/2009 | Kotter et al. |
| 2009/0212217 | A1 | 8/2009 | Mann et al. |
| 2009/0272906 | A1 | 11/2009 | Gratton |
| 2010/0044570 | A1 * | 2/2010 | McGill et al. ............. 250/338.5 |
| 2010/0067844 | A1 | 3/2010 | Sanders |
| 2010/0284086 | A1 | 11/2010 | Novack et al. |
| 2011/0277805 | A1 * | 11/2011 | Novack et al. ............... 136/243 |
| 2011/0315880 | A1 | 12/2011 | Nemirovsky |
| 2012/0153168 | A1 | 6/2012 | Langeveld |
| 2012/0175521 | A1 * | 7/2012 | Chawla .................... 250/339.02 |
| 2012/0224167 | A1 | 9/2012 | Sanders et al. |
| 2012/0305773 | A1 | 12/2012 | Wu et al. |

OTHER PUBLICATIONS

Kotter et al., "Lithographic Antennas for Enhancement of Solar-Cell Efficiency," Idaho National Engineering Laboratory, INEEL/EXT-98-00389, Apr. 1998, 26 pages.

Remski et al., "Frequency Selective Surfaces," Design and Analysis Using the Ansoft Product Suite, Ansoft Corporation, Presentation #4, 34 pages, 2000.

U.S. Appl. No. 13/426,407, filed Mar. 21, 2012, titled "Apparatuses and Method for Converting Electromagnetic Radiation to Direct Current," to Kotter et al.

U.S. Appl. No. 13/601,592, filed Aug. 31, 2012, titled "Energy Harvesting Devices, Systems, and Related Methods," to Dale K. Kotter.

U.S. Appl. No. 60/987,630, filed Nov. 13, 2007, titled "Antenna Devices Comprising Flexible Substrates, Related Structures, and Methods of Making and Using the Same," to Pinhero et al.

International Search Report for International Application No. PCT/US2013/077561, dated Mar. 27, 2015, 2 pages.

International Written Opinion for International Application No. PCT/US2013/077561, dated Mar. 27, 2015, 6 pages.

* cited by examiner

TERAHERTZ IMAGING DEVICES AND SYSTEMS, AND RELATED METHODS, FOR DETECTION OF MATERIALS

GOVERNMENT RIGHTS

This invention was made with government support under Contract Number DE-AC07-05ID14517 awarded by the United States Department of Energy. The government has certain rights in the invention.

FIELD

Embodiments of the present disclosure relate to radiation sensitive devices and systems and methods for detection of certain materials using such devices and systems. In particular, embodiments of the present disclosure relate to terahertz imaging devices and threat detection systems including an array of resonance elements configured to exhibit a resonant frequency in the terahertz range.

BACKGROUND

There is a security interest in detecting threatening materials, such as radioactive materials, explosives, etc., at airports, seaports, border crossings, public places, and other locations. Conventionally, radiation detectors for identifying materials such as radioactive materials, explosives, etc., are effective only in close proximity to the material because radiation intensity drops at a rate proportional to $1/r^2$, where r is the distance between the material and the radiation detector. Thus, conventional detection methods are relatively ineffective in standoff detection scenarios where detectors are located a substantial distance from containers, cargo, land vehicles and watercraft to be scanned for threatening materials.

Radiation detection methods are primarily reliant on ionization and scintillation processes, which often require high-voltage biasing and/or electro-optical assemblies that may be electrically and mechanically complex. Such radiation detectors may also be too bulky, be too fragile, have a relatively low-power output, and have a relatively low signal to noise ratio (SNR), which often make conventional radiation detectors unsuited for field deployment, where there exists a relatively high level of thermal background and atmospheric attenuation. In addition, such radiation detectors may also require cryogenic cooling.

Inorganic scintillators, for example, exhibit a nonlinear response and poor energy resolution, which limits their use for high-resolution spectroscopic applications. Some conventional radiation detectors require the growth of crystals that are expensive and fragile. Furthermore, many conventional neutron detectors do not have capability to provide imaging or directional information.

Radiation detection in the terahertz (THz) region has faced several issues in terms of conventional THz sources or detectors. The conventional THz sources may include ultrafast laser switches, pumped gas lasers, optical difference generation techniques, frequency doubling diodes and quantum cascade lasers. Such components may require cumbersome equipment and large power sources. As a result, conventional methods that use time domain THz spectroscopy require a laser scanning system with fragile optical components, do not provide real-time analysis, are expensive, and are not readily adapted to field use. Other radiation detection systems, such as ion mobility spectrometers may require a small sample of the material (e.g., explosive material) to be physically brought to the ion mobility spectrometer for analysis. As a result, conventional methods of radiation detection may be less efficient, relatively expensive, and time consuming.

Turning to another technology, frequency selective surfaces (FSS) are used in a wide variety of applications including radomes, dichroic surfaces, circuit analog absorbers, and meanderline polarizers. An FSS may be any surface construction designed as a "filter" for plane waves with angular/frequency dependence and a bandpass/bandstop behavior. For example, an FSS may comprise a two-dimensional periodic array of electromagnetic antenna elements. Such antenna elements may be in the form of, for example, conductive dipoles, loops, patches, slots or other antenna elements. FSS structures generally include a metallic grid of antenna elements formed on a dielectric substrate. Each of the antenna elements within the grid defines a receiving unit cell. An electromagnetic wave incident on the FSS structure will pass through, be reflected by, or be absorbed by the FSS structure. This behavior of the FSS structure generally depends on the electromagnetic characteristics of the antenna elements, which can act as resonance elements. As a result, the FSS structure can be configured to function as low-pass, high-pass, or dichroic filters. Thus, the antenna elements may be designed with different geometries and different materials to generate different spectral responses.

DETAILED DESCRIPTION

Figure 1:
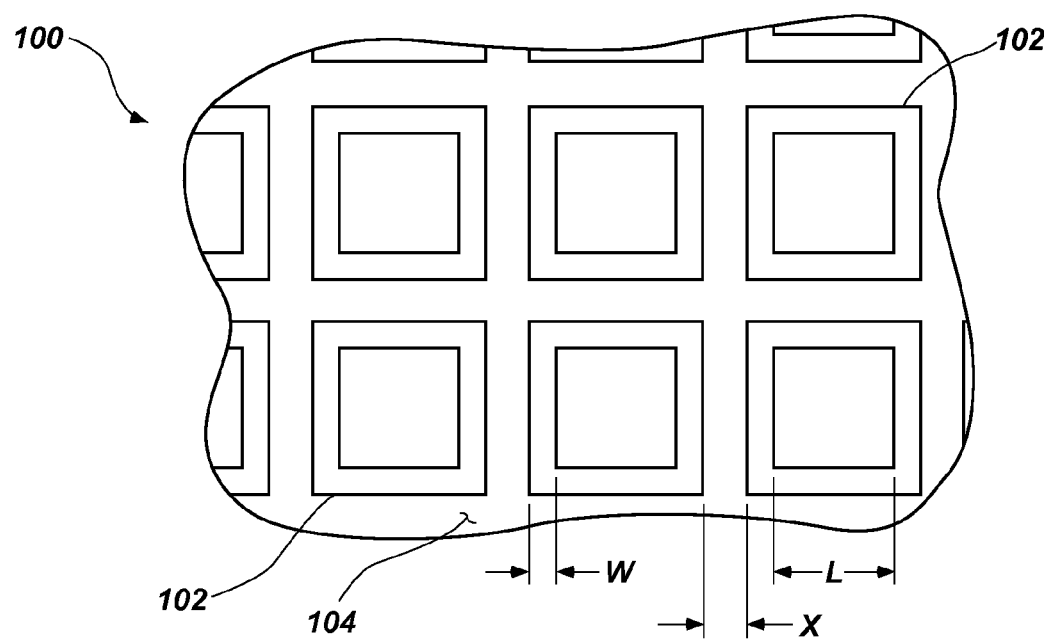
FIG. 1 is a partial plan view of a terahertz imaging device including various resonance structures or elements coupled to a substrate.

In the following detailed description, reference is made to the accompanying drawings that form a part hereof, and in which is shown by way of illustration specific embodiments of the present disclosure. These embodiments are described with specific details to clearly describe the embodiments of the present disclosure. However, the description and the specific examples, while indicating examples of embodiments of the present disclosure, are given by way of illustration only and not by way of limitation. Other embodiments may be utilized and changes may be made without departing from the scope of the disclosure. Various substitutions, modifications, additions, rearrangements, or combinations thereof may be made and will become apparent to those of ordinary skill in the art. In addition, features from one embodiment may be combined with features of another embodiment while still being encompassed within the scope of the disclosure as contemplated by the inventor.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed or that the first element must precede the second element in some manner. In addition, unless stated otherwise, a set of elements may comprise one or more elements.

As used herein, the term "radiation" refers to one or more of energetic particles (e.g., alpha particles, beta particles, neutrons) and energetic waves (e.g., gamma rays, infrared (IR) light, THz waves, other light, etc.).

As defined herein, the term "THz range" is defined herein as frequencies of approximately 0.1 THz to approximately 4 THz. In other words, a "THz frequency" is a frequency that is within the THz range. The frequency range for some explosive materials of interest may be within a range of approximately 0.1 THz to approximately 3 THz. Accordingly, depending on the object(s) of interest for a particular application, the range of actual operation may be a sub-set of the overall THz range defined herein. THz radiation's relatively low photon energy levels allow the imaging of biological tissue without harmful ionizing radiation, making THz radiation safer than X-rays. The unique vibrational, rotational, and translational responses of materials within the THz range provide information generally absent in optical, X-ray and NMR images, enabling a sort of THz wave fingerprint of the molecular structure of the material being imaged.

Embodiments of the present disclosure include methods for collecting, concentrating, and converting incident THz energy to a quantifiable DC signal for further image processing. As a result, embodiments of the present disclosure may employ THz radiation for visual imaging and/or spectroscopy of hidden items, such as threat objects. Compared to microwaves, THz waves have more energy, which may cause THz waves to penetrate deeper and result in sharper images due to their shorter wavelength. Embodiments of the present disclosure may be particularly well-suited for detection of biological weapons and explosive materials within packaging, briefcases, or under clothing because of the penetrating nature of THz waves.

THz waves may be scattered less than visible and near infrared frequencies, as the amount of Rayleigh scattering decreases with the fourth power of the wavelength. Unlike other types of penetrating radiation currently used for detecting hidden explosives and weapons (e.g., X-ray, neutron interrogation, etc.), THz radiation is non-ionizing. As a result, THz radiation may not present health hazards at the power levels used. Embodiments of the present disclosure include THz imaging and/or TH spectroscopy on various materials (e.g., explosive materials), which may be identified by unique spectral features (e.g., absorption peaks, peak widths, ratio between peak heights, etc.) of the material that can serve as discriminators of threat materials.

It is recognized that environmental conditions may hinder standoff detection in the THz region. There are multiple regions of water absorption peaks in the atmosphere and a high infrared thermal background. Embodiments of the present disclosure may improve the SNR of the detected signal, and increase the standoff distance for detection.

Radiation sensitive devices of the present disclosure may include an array or other periodic arrangement of resonance elements, which also may be referred to as antennas, microantennas, nanoantennas, and nanoparticles. The radiation sensitive devices may include, but are not limited to, FSS structures. Generally, the radiation sensitive devices may include conductive resonance elements formed in a specific pattern and coupled to a substrate. The resonant properties of the radiation sensitive devices are largely dependent on the structure's layout in terms of shape, dimensions, periodicity, the structure's material properties, and electro-optical parameters of surrounding media. Thus, the resonance elements of the radiation sensitive devices may have a peak resonance. By varying the device geometry, material properties, or combinations thereof, the resonance of an FSS structure may be tuned to meet specific design requirements.

Embodiments of the present disclosure include THz imaging devices and systems. Such THz imaging devices and systems may be used for the positive identification of explosive materials, biological materials that have natural absorption spectra in the THz range. For example, embodiments of the present disclosure may be employed as enabling technology for military applications, such as stand-off detection of explosives (e.g., improvised explosive devices ((IED)), for homeland defense and law enforcement applications, such as security systems, for biological threat detection, and other related applications. Embodiments of the disclosure may be employed within the mail system, which may be used to determine whether a package or letter contains spores or other dangerous material. Additional threats that may be detectable by embodiments of the disclosure include concealed weapons (e.g., guns, knives, etc.), including those that are made out of non-metallic, non-polar materials that may not be detectable by current airport security systems.

Embodiments of the present disclosure may be used to detect harmful biological or chemical agents. Examples of chemical weapons that may have THz signatures include: blistering agents like chlorine gas and mustard gas that burns and destroys lung tissue; chemical weapons that include chemicals often found in insecticides; various nerve agents such as sarin gas, cyclosarin, soman, canisters of CS gas, a gas similar to tear gas, etc. Examples of biological weapons that may have THz signatures include bacteria or virus that form spores, such as anthrax bacteria; or bacteria that releases toxins that have a chemical fingerprint, such as botulinum.

In addition, embodiments of the present disclosure may be employed in biomedical imaging and genetic diagnostics applications. For example, THz imaging may improve detection of breast cancer through sharper imaging and molecular fingerprinting, as well as imaging and diagnostic techniques for skin cancer, skin burn severity, and even tooth cavities.

FIG. 1 is a partial plan view of a terahertz imaging device 100 including various resonance structures or elements 102 coupled to a substrate 104. The radiation sensitive device 100 may include an array of resonance elements 102 (e.g., nanoantennas, nanoparticles) coupled to (e.g., positioned on or at least partially in) a substrate 104. The resonance elements 102 may be disposed on a top surface of the substrate 104. In other embodiments, the resonance elements 102 may be partially or fully disposed within the substrate 104. The radiation sensitive device 100 may also include a ground plane (not shown) coupled with the substrate 104 on the opposite side as the resonance elements 102. The distance between the resonance elements 102 and the ground plane may be approximately one quarter of the wavelength of the resonant frequency of the resonance elements 102 to provide an optical resonance gap for reflected radiation from the ground plane. The ground plane may, therefore, be formed from materials exhibiting relatively good reflective properties, such as gold (Au) or copper (Cu).

The radiation sensitive device 100 may include resonance elements 102 configured to resonate responsive to incident radiation having a desired frequency within the terahertz (THz) range. In other words, the resonance elements 102 may be configured to exhibit a resonant frequency for a frequency of interest in the THz range. For example, a designer may have several degrees of freedom in tailoring the resonance elements 102 to a frequency of interest. For example, the shape, dimensions (e.g., length (L), width (W)), spacing (denoted as X) between resonance elements 102, materials used, orientation, etc., may contribute to the resonant frequency.

The radiation source may be a so-called "passive" radiation source or a so-called "active" radiation source. Passive radiation sources generally include radiation sources that exist in the environment. In other words, the incident radiation from a passive radiation source may come from an object of interest without the aid of outside THz light source exciting the object. For example, an explosive material may be a passive radiation source that provides incident radiation to the radiation sensitive device 100. Active radiation sources include radiation sources that are actively provided for the purpose of inducing resonance of the resonance elements 102 or to induce the object of interest to absorb the active radiation and emit THz radiation that has characteristics that may be detected. For example, a laser (e.g., an IR laser), a light-emitting diode (LED) (e.g., an IR LED), or a radar may be used as the active radiation source from which incident radiation may be directed toward an object of interest to induce absorption and excitation of radiation by the object of interest. For example, organic molecules of explosive materials may have unique vibrational and rotational frequencies that the rotational frequencies lie in the THz range, which may be excited by THz waves within the molecules of explosive materials. Thus, the resonance elements 102 of the radiation sensitive device 100 may be configured to produce the output signal (e.g., resonate) in response to radiation from one or both of an active and a passive radiation source.

In the embodiment described with respect to FIG. 1, the resonance elements 102 are shown as exhibiting substantially square loop geometries. However, the geometries (e.g., shape, size, and layout) of the resonance elements 102 may be modified according to the particular application, and the example embodiments described herein are not limiting with respect to such potential geometries. Thus, the geometries of the resonance elements 102 may be tailored (e.g., tuned) to absorb incident radiation in a range of wavelengths and resonate at a particular wavelength responsive to the absorbed incident radiation. For example, the shape of each resonance element 102 may be a simple dipole, a bowtie dipole, a spiral, a square loop, a square spiral, a circular loop, concentric loops, an ellipse, a rectangle, a triangle, a cross, or any other shape designed to absorb incident radiation and resonate responsive thereto at a given wavelength. The resonance wavelength of the resonance elements 102 may be tailored (e.g., tuned) by altering the geometries and materials of the resonance elements 102 and other components of the radiation sensitive device 100. In response to the resonance elements 102 absorbing the incident radiation and resonating, the resonance elements 102 may generate an output signal having a frequency that is approximately the resonant frequency of the resonance elements 102. In some embodiments, each resonance element 102 may be coupled with an energy transfer element, such as a diode configured to act as a rectifier.

The resonance elements 102 may be formed of an electrically conductive material. The conductive material of the resonance elements 102 may include, for example, one or more of manganese (Mn), gold (Au), silver (Ag), chromium (Cr), copper (Cu), aluminum (Al), platinum (Pt), nickel (Ni), iron (Fe), lead (Pb), and tin (Sn), titanium (Ti), or any other suitable electrically conductive material. In one embodiment, the conductivity of the material used to form the resonance elements 102 may be from approximately $1.0\times10^6$ $Ohms^{-1}$-$cm^{-1}$ to approximately $106.0\times10^6$ $Ohms^{-1}$-$cm^{-1}$. The resonance elements 102 may be formed by known methods of fabrication that are not described in the present disclosure in detail. By way of non-limiting examples, the resonance elements 102 may be formed by at least one of sputtering, electroplating, chemical vapor deposition (CVD), imprint lithography, photolithography, or any other appropriate technique chosen by one of ordinary skill in the art for forming a conductive material on a substrate.

The substrate 104 may include a dielectric material. As non-limiting examples, the substrate 104 may comprise a semiconductor-based material including silicon, silicon-on-insulator (SOI) or silicon-on-sapphire (SOS) technology, doped and undoped semiconductor materials, epitaxial layers of silicon supported by a base semiconductor foundation, and other semiconductor structures. In addition, the semiconductor material need not be silicon-based, but may be based on silicon-germanium, silicon-on-insulator, silicon-on-sapphire, germanium, or gallium arsenide, among others. For example, the substrate 104 may include one or more of an elemental semiconductor material (e.g., silicon, germanium, antimony, etc.), a binary compound semiconductor material (e.g., SiGe, SiC, InSb, InAs, GaP, AlSb, GaN, GaAs, CdTe, etc.), and a tertiary compound semiconductor material (e.g., HgCdTe, InGaAs, CdZnTe, HgBrI, etc.). In some embodiments, the substrate 104 may comprise a flexible material selected to be compatible with energy transmission of a desired wavelength, or range of wavelengths, of light. The substrate 104 may be formed from a variety of flexible materials such as a thermoplastic polymer or a moldable plastic. By way of other non-limiting examples, the substrate 104 may comprise polyethylene, polypropylene, acrylic, fluoropolymer, polystyrene, poly methylmethacrylate (PMMA), polyethylene terephthalate (MYLAR®), polyimide (e.g., KAPTON®), polyolefin, quartz, or any other material suitable for use as a substrate 104. In additional embodiments, the substrate 104 may comprise a binder with nanoparticles distributed therein, such as silicon nanoparticles distributed in a polyethylene binder, or ceramic nanoparticles distributed in an acrylic binder. Any type of substrate 104 may be used as long as it is compatible with the transmission of a desired wavelength within the spectrum of electromagnetic radiation.

Methods used to analyze and design the components of the radiation sensitive device 100 include modeling techniques known in the art, such as, by way of example, a Periodic Method of Moments (PMM) analysis and/or a finite element analysis (FEA). A PMM analysis may take into consideration a number of different variables, such as anticipated operational wavelengths, material properties, component geometries, and component dimensions, as is known in the art. For example, generally, the resonant frequency or frequencies of the resonance elements 102 may be determined in part by the size, shape, spacing, and material properties of the resonance elements 102, as well as by the configuration and properties of surrounding materials, such as of the substrate 104 and the ground plane (not shown).

Figure 2:
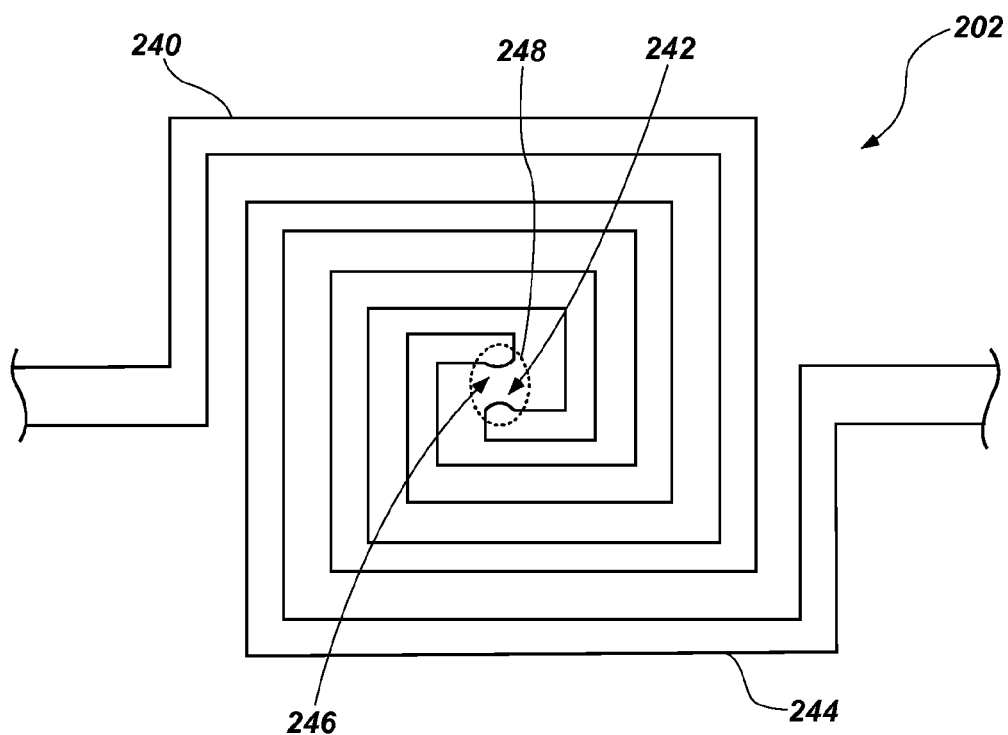
FIG. 2 is a plan view of a resonance element according to an embodiment of the present disclosure.

FIG. 2 is plan view of a resonance element 202 according to another embodiment of the present disclosure. The resonance element 202 may be configured according to a geometry that may be referred to as "square spirals" or "angular spirals." Such a geometry may include a first portion 240 that spirals inwardly to a termination point 242 and a second portion 244 that is essentially a reversed image (both vertically and horizontally) and spirals inwardly to a termination point 246. The first portion 240 and the second portion 244 are cooperatively interleaved with one another such that their respective termination points 242 and 246 are positioned proximate one another. The termination points 242, 246 may act as feedpoints for an energy transfer element 248, which will be further described hereinbelow.

In operation, the resonance element 202 responds to incident radiation, which induces a THz current signal to flow in the first portion 240 and the second portion 244 of the resonance element 202. The THz current signal may generate a sinusoidal voltage at each of the termination points 242, 246. Thus, the resonance element 202 may be configured to concentrate energy at the termination points 242, 246. A rectifier (not shown) may be coupled at the termination points 242, 246 to convert the alternating current (AC) signal to a direct current (DC) signal. The resonance element 202 may be arranged in an array with other resonance elements 202 to form a focal plane array used for imaging and spectroscopy devices described below.

Figure 3:
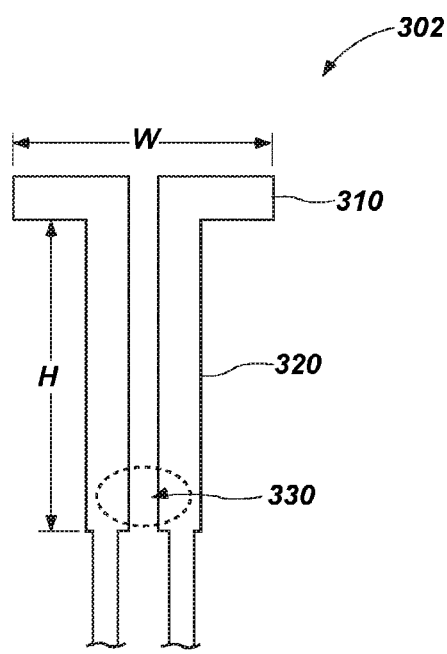
FIG. 3 is a plan view of a resonance element.

FIG. 3 is a plan view of a resonance element 302 that includes a dipole antenna 310, coplanar strips (CPS) 320, and an energy transfer device 330. The CPS 320 couple the dipole antenna 310 and the energy transfer device 330. In operation, incident THz radiation excites surface AC current waves in the dipole antenna 310, which are fed to the energy transfer device 330 via the CPS 320. The AC current waves are rectified by the energy transfer device 330 to DC current for further signal processing.

In some embodiments, the energy transfer device 330 may include a detector that is integrated into the antenna structure, such as being integrated into the antenna feedpoint. As a result, such a configuration may be referred to herein as an "antenna coupled detector." The detector may be one of various sensor types configured to measure and/or convert the high-frequency voltage generated in the resonance element 302 responsive to the incident THz radiation. Examples of such sensor types include bolometers, tunnel junctions and Schottky diodes, MIM diodes, etc.

A bolometer may include a material (e.g., bismuth) that is embedded into the antenna feedpoint. The bolometer is configured to convert THz energy to a corresponding DC current. The generated DC current may be monitored, using various methods, to provide an indicator of energy in the THz bands. A diode may serve as a half-wave rectifier to convert the THz energy (an AC signal) to generate DC current that may be monitored by data acquisition components to provide an indicator of energy in the THz bands. The diode may include an antenna-coupled metal-insulator-metal (MIM) diode that provides detection of the incoming THz wave. The MIM diode may include a thin insulator material (e.g., an oxide) sandwiched between two metal electrodes that have contrasting work functions. The MIM diode may be enabled when a large enough field causes the tunneling of electrons across the insulator material.

The MIM diode may be of a size that makes it behave as a lumped device. The sub-micron sized diode junction area may exhibit low enough junction capacitance to sustain THz-rate switching times. The sheet resistance of the metal electrodes may be controlled through sputter deposition, to achieve proper impedance matching between the antenna and the transmission line. Impedance matching may ensure maximum power transfer between components and, thus, to minimize reflection losses.

The MIM diode may be fabricated with the resonance element 302 through electron-beam lithography and conventional sputtering techniques. The anode and cathode of the MIM diode may be selected from the group consisting of aluminum (Al), chromium (Cr), niobium (Nb), nickel (Ni), silver (Ag), and platinum (Pt). The insulator of the MIM diode may be selected from the group consisting of CrO, $Al_2O_3$, NbOx, and NiO.

Figure 4:
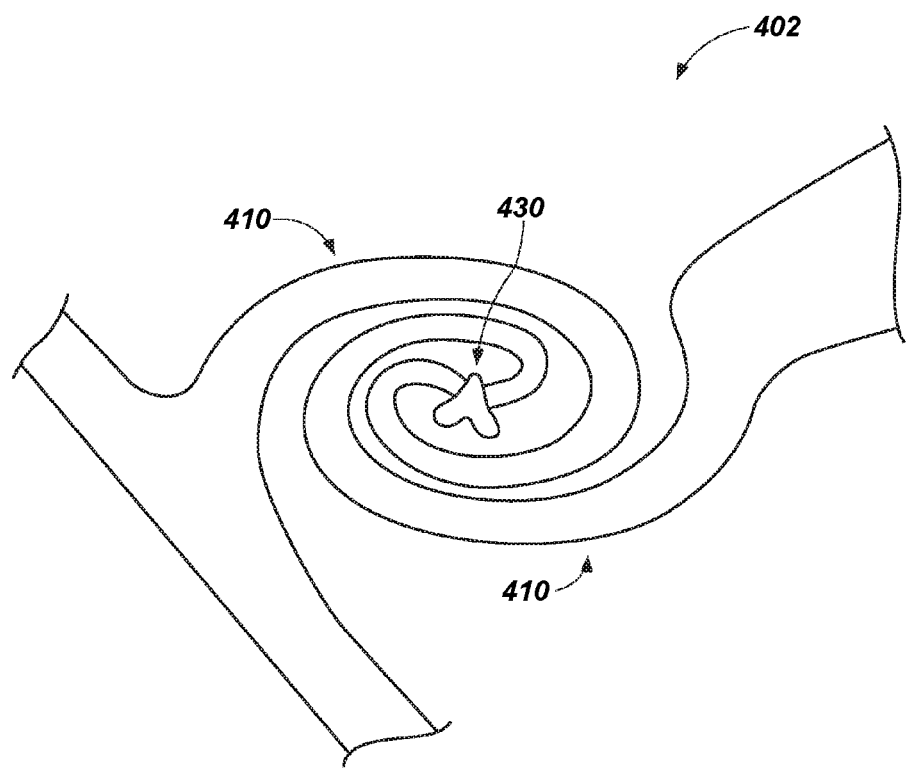
FIG. 4 is a plan view of a resonance element configured as a broadband spiral antenna.

FIG. 4 is a plan view of a resonance element 402 configured as a broadband spiral antenna. The resonance element 402 may include a plurality of arms 410 that are operably coupled to an energy transfer device 430. The ends of the plurality of arms 410 may feed to a common feedpoint and couple to the energy transfer device 430. The energy transfer device 430 may include a bolometer, a diode, and other detection and/or rectification elements configured to generate a DC current indicating energy in the THz bands responsive to the incident THz radiation. Thus, the resonance element 402 may be an antenna-coupled detector that directs the AC signal generated responsive to the incident radiation to the energy transfer device to rectify the AC signal to generate a DC signal for further analysis. In some embodiments, the energy transfer device 430 may be a diode, such as a tunnel diode, a Schottky diode, and an MIM diode. Such diodes may be less lossy relative to bolometers, which for some embodiments may be used for detecting low concentration and low-vapor pressure explosives (e.g., Research Department Explosive (RDX), trinitrotoluene (TNT)).

The resonance elements 102 (FIG. 1), 202 (FIG. 2), 302 (FIG. 3), and 402 (FIG. 4) may be part of a larger focal point array of an imaging device. In particular, each resonance element may be an individual pixel of the focal point array (FIG. 5), which will be described more in more detail below. Further details regarding additional resonance elements are described in U.S. Pat. No. 8,071,931, filed Nov. 13, 2007, and issued Dec. 6, 2011, and in U.S. patent application Ser. No. 13/771,905, filed on the same day as the present application, and entitled "Radiation Sensitive Devices and Systems for Detection of Radioactive Materials and Related Methods," the disclosure of each of which is incorporated herein in its entirety by this reference.

Figure 5:
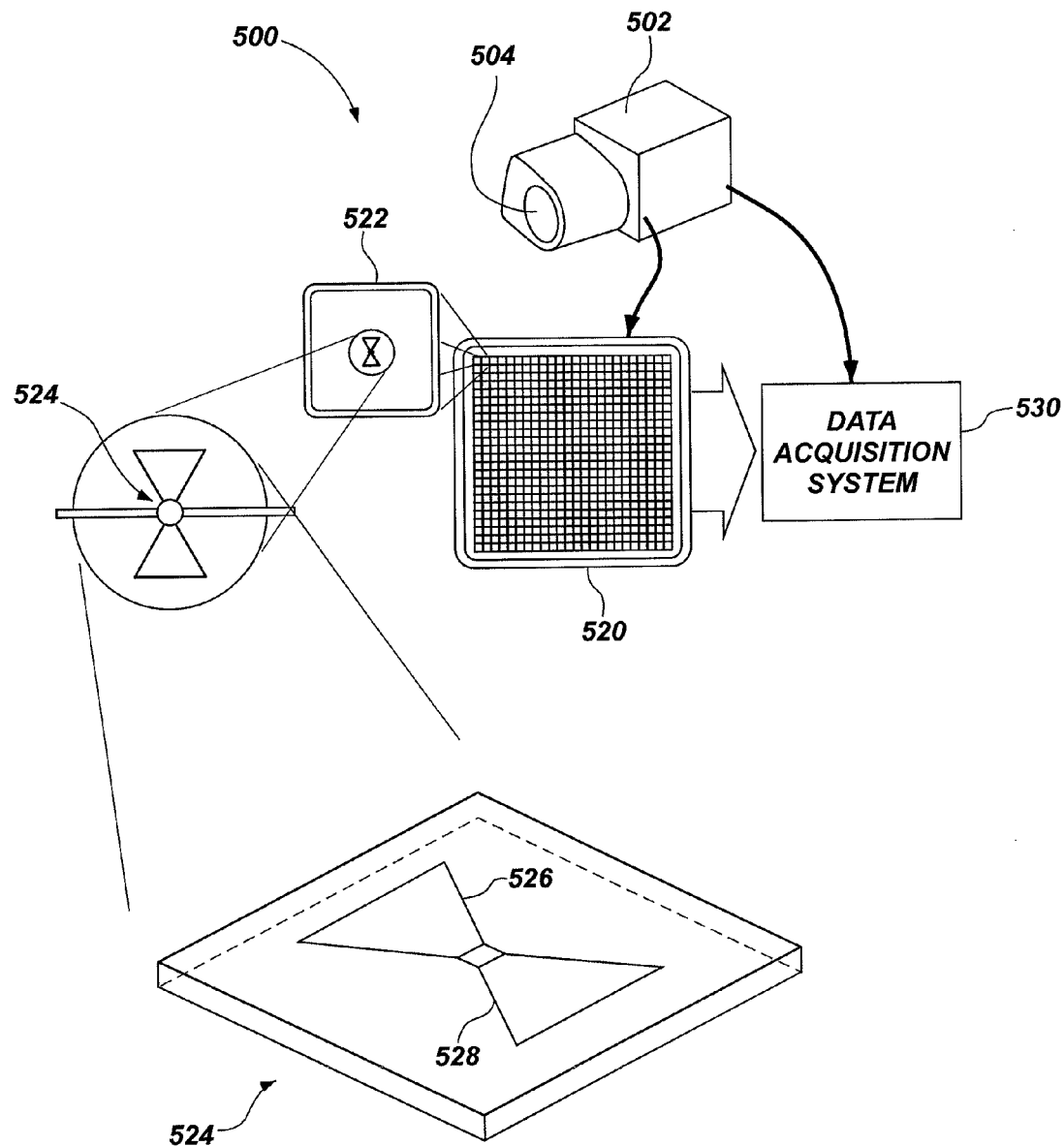
FIG. 5 is an imaging system according to an embodiment of the present disclosure.

FIG. 5 is an imaging system 500 according to an embodiment of the present disclosure. The imaging system 500 includes a portable THz imaging device 502. The portable THz imaging device 502 may include a lens 504 through which incident radiation may be received. The portable THz imaging device 502 may further include a focal plane array 520 and a data acquisition system 530. The focal plane array 520 may be configured to generate a data signal in response to the incident radiation. The focal plane array 520 may generate the data for a plurality of pixels 522 arranged in an array format. FIG. 5 shows a zoomed-in, enlarged, view of one of the pixels 522 of the focal plane array 520. Each pixel 522 may include resonance elements 524 (e.g., antenna-coupled detectors) that are configured to exhibit a resonance frequency that is tuned to a THz frequency. FIG. 5 also shows a zoomed-in, enlarged, view of one of the resonance elements 524 of the pixel 522.

In the embodiment shown in FIG. 5, the resonance element 524 may be configured as a bowtie dipole antenna. The bowtie configuration may include a plurality of arms 526, 528 that have an outer width that is greater than an inner width. The plurality of arms 526, 528 may be separated by a port gap width, within which a diode may be coupled to the resonance element 524 to generate a DC output voltage. The resonance element 524 may be configured to exhibit a resonant frequency that is tuned to particular frequency of interest. As a non-limiting example, the resonance element 524 may be tuned to exhibit a resonant frequency of approximately 0.8 THz (which is approximately one of the peaks of RDX). To achieve such a resonant frequency, the inner width may be approximately 2.41 µm, the outer width may be approximately 43.36 µm, the arm length may be approximately 48.16 µm, the port gap width may be approximately 2.41 µm, and the substrate thickness may be approximately 62 mil. Other combinations of dimensions may likewise achieve the desired resonant frequency. For example, the focal plane array 520 may have a general range of being about 1,000 µm to about 10,000 µm, the pixel 522 may have a general range of being about 20 µm to about 80 µm, the resonance element 524 may have a general range of about 5 µm to about 15 µm. In some embodiments, an energy transfer device of the resonance element 524 may be about 50 nm to about 200 nm.

The data signal output from the focal plane array 520 may include a DC voltage as data from each pixel 522. The data acquisition system 530 may also be configured to perform data analysis and reconstruct an image based on the value of the data in each pixel 522. As an example, the focal plane array 520 may be configured as a 320 pixel×240 pixel array with the associated data acquisition system 530 to digitize the THz image. For real-time imaging, a frame rate may be approximately a 30 Hz frame rate or greater. The portable THz imaging device 502 may be configured as a passive device that receives incident radiation that is emitted from an object. In operation, if the incident radiation exhibits frequencies that are approximately the same as the resonant frequency of the resonance elements 524, the resonance elements 524 may generate the output signal.

In some embodiments, the focal plane array 520 may be subdivided into a plurality of resonance elements 524 having a plurality of different resonant frequencies. For example, a first portion of the focal plane array 520 may be tuned to a detect a particular type of explosive (e.g., RDX), a second portion of the focal plane array 520 may be tuned to detect another explosive (e.g., TNT), and so on. Additional sub-arrays may be tuned to exhibit different resonant frequencies to detect other materials.

In addition, sub-arrays of the focal plane array 520 may be tuned to a plurality of different spectral absorption peaks for the radiation from the same material. For example, RDX may exhibit a spectral response having spectral absorption peaks at approximately 0.82 THz, 1.05 THz, 1.50 THz, 1.96 THz, 2.20 THz, and 3.08 THz. Thus, different sub-arrays of the focal plane array 520 may be tuned to one or more of these spectral absorption peaks. For example, a first sub-array of the focal plane array 520 may have a narrow response tailored to approximately 0.82 THz, a second sub-array of the focal plane array 520 may have a narrow response tailored at approximately 1.05 THz, and so on. As a result, if an output signal is generated by a plurality of the sub-arrays tuned as such, the likelihood of false positives being detected may be reduced than if the entire array is tuned to only one of the spectral absorption peaks.

Embodiments of the present disclosure may include a focal plane array 520 that may be tuned to a single frequency or frequency range, or that may be divided into sub-arrays tuned at different frequencies that act as separate windows to detect energy levels occurring at that specific tuned frequency. The outputs from each of the sub-arrays may be effectively a digital response for a narrowly-tuned frequency. For example, if a narrowly-tuned sub-array generates an output, it may be determined that a spectral absorption peak occurs at that frequency. As a result, the material (e.g., explosive) may be determined, because the material that is present will have a spectral absorption peak that occurs at the frequency to which the sub-array has been tuned. Continuing the example of RDX, there may be at spectral absorption peaks at approximately the six frequencies listed above. The focal plane array 520 may have narrowly tuned sub-arrays at one or more of these frequencies. If the focal plane array 520 includes sub-arrays tuned to each of these frequencies, then at least six different sub-arrays may be present. If an output is generated from each of the plurality of different sub-arrays that are tuned to the spectral absorption peaks, it may be determined that a material may have multiple absorption peaks within each of the regions of the sub-arrays. Of course, other sub-arrays may be present that are tailored to detect spectral absorption peaks for other materials.

Figure 6A:
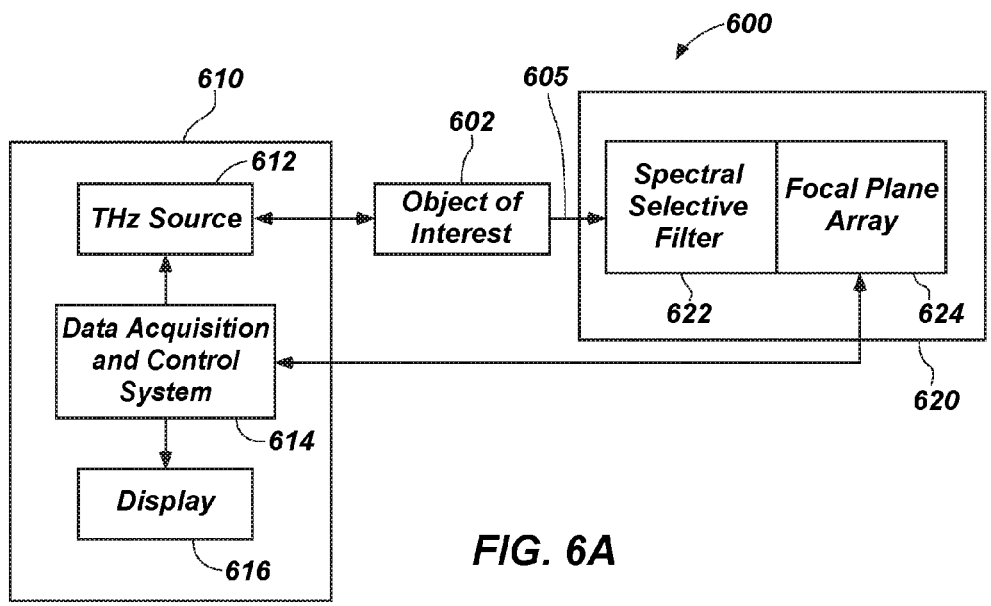
FIG. 6A is a schematic block diagram of a THz imaging and spectroscopic analysis system according to another embodiment of the present disclosure.
Figure 6B:
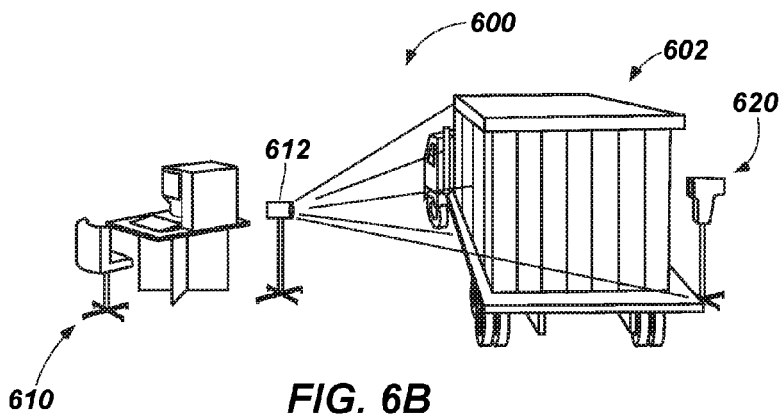
FIGS. 6B and 6C show different arrangements of the THz imaging and spectroscopic analysis system of FIG. 6A.
Figure 6C:
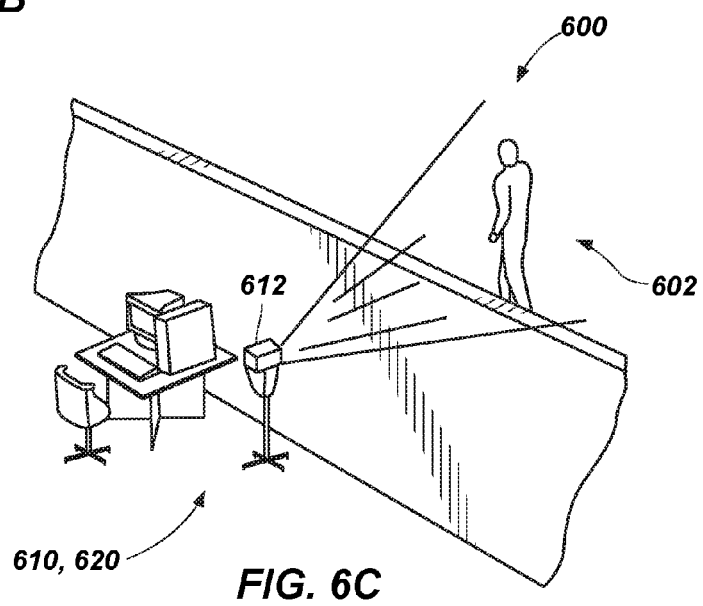

FIG. 6A is a schematic block diagram of a THz imaging and spectroscopic analysis system 600 according to another embodiment of the present disclosure. FIGS. 6B and 6C show different arrangements of the THz imaging and spectroscopic analysis system 600. The THz imaging and spectroscopic analysis system 600 includes a control system 610 and a detector system 620. The control system 610 includes a THz source 612, a data acquisition and control system 614, and a display 616. The detector system 620 includes a THz spectral selective filter 622 and a focal plane array 624. The THz imaging and spectroscopic analysis system 600 may be configured to perform concurrent broad-band imaging and spectroscopy of an object of interest 602. The THz imaging and spectroscopic analysis system 600 may be configured to operate at room temperature without the need for cryogenic or thermoelectric cooling of the detector system 620.

The THz imaging and spectroscopic analysis system 600 may be configured as an active device that transmits radiation (from THz source 612) toward an object of interest 602 to induce radiation to be emitted therefrom. In other words, the THz source 612 may be used to illuminate the object of interest 602 with specific energies that induce rotational and vibrational molecular excitation of the suspected explosive material. The THz source 612 may include one or more diodes and far-infrared filters configured to block the IR signals and pass the THz signals. For example, a fixed far-infrared long wave-pass filter may be mounted on a blackbody radiator to tailor the spectral emissions from the THz source 612. Thus, a standard blackbody source may be employed without the THz frequencies being swamped out by IR background, which may result in a relatively simpler and cheaper system. For example, the THz source 612 may include a continuous wave (CW) broadband THz diode, such as a varactor nonlinear diode configured in a frequency multiplier circuit generating a THz signal. Such an "active mode" may reduce impacts from atmospheric attenuation and improve stand-off detection.

The detector system 620 may be tuned to the spectral fingerprint of interest. The focal plane array 624 may be configured generally, as described above, with respect to FIG. 5. For example, the focal plane array 624 may include a plurality of pixels that include a resonance element tuned for a particular frequency of interest or a particular band of frequencies of interest. The resonance elements may include a detector (e.g., energy transfer elements) integrated into the antenna structure of the resonance elements. Each pixel of the focal plane array 624 may include both spectroscopic and image information.

The spectral selective filter 622 may be configured as a narrow bandpass filter to allow radiation of a specific frequency to pass therethrough. As a result, the spectral selective filter 622 may be placed over the lens for the focal plane array 624 in the path of incident radiation 605. The spectral selective filter 622 may include a nano-antenna to focus energy at very discrete bands. For example, at 1.1 microns, energy may have a greater probability of passing through the atmosphere. Therefore, the spectral selective filter 622 may be configured to concentrate energy into that band. As a result, the focal plane array 624 may receive the specific energy that passes through the spectral selective filter 622 and ignore the energy that does not pass through the spectral selective filter 622. If the THz source 612 and the focal plane array 624 are configured to operate within the same frequency space, obtaining a proper output signal may be more likely.

By integrating the spectral selective filter 622 as a front lens to the focal plane array 624, the THz imaging and spectroscopic analysis system 600 may concurrently perform THz imaging and spectroscopic material characterization. As a result, a THz camera may be configured to provide THz imagery of concealed threats plus spectral selective detection and analysis of explosive vapors. Additional detail regarding the spectral selective filter 622 is discussed below.

The data acquisition and control system 614 may be a computer that is configured to acquire the data from the focal plane array 624 and implement the matched filter analysis. In some embodiments, the data acquisition and control system 614 may include a single-board computer or an embedded controller to acquire spectra and to implement the matched filter analysis.

In operation, the object of interest 602 absorbs the radiation from the THz source 612, and emits radiation, which may be detected by the focal plane array 624. If the incident radiation 605 received by the focal plane array 624 exhibits frequencies that are approximately the same as the resonant frequency of the resonance elements, the resonance elements may generate the output signal. Therefore, as discussed above, the resonance elements of the focal plane array 624 may be configured to have a resonant frequency that is tuned to one or more spectral peaks for one or more radiation sources of interest. The signature of the illuminated object of interest 602 may be measured in a back scatter mode (FIG. 6B) or a reflection mode (FIG. 6C). In back scatter mode, the THz source 612 and the detector system 620 may be positioned on the opposite side of the object of interest 602 such that the back scatter radiation is received by the detector system 620. In reflection mode, the THz source 612 and the detector system 620 may be positioned on the same side of the object of interest 602 such that the reflected radiation is received by the detector system 620.

In some embodiments, the focal plane array 624 may be tuned for operation in a broader band than the spectral selective filter 622. As an example, the focal plane array 624 may be tuned for a broader band, such as having elements that resonate at frequencies between 0.1 THz to 3.0 THz. The spectral selective filter 622 may be used for narrow band selectivity for absorption lines of pre-defined chemical specie. As a result, the SNR may be improved by reducing interferences in the incident radiation 605 received by the focal plane array 624. As a result, the distance for standoff from the object of interest 602 may be increased. For a passive system, the standoff may be about 30 meters in some embodiments.

In some embodiments, the detector system 620 may include the data acquisition and control system 614 within (or attached to) the same form factor (i.e., housing) as the focal plane array 624. The spectral selective filter 622 may be formed with, or attached to the housing as well. Thus, the detector system 620 including the spectral selective filter 622, focal plane array 624, and data acquisition and control system 614 may be configured as a portable (e.g., handheld) device for easy transportation and use by a technician in the field. The THz source 612 may also be a separate portable (e.g., handheld) device that may be transported and arranged relatively easily by a technician in the field.

Figure 7:
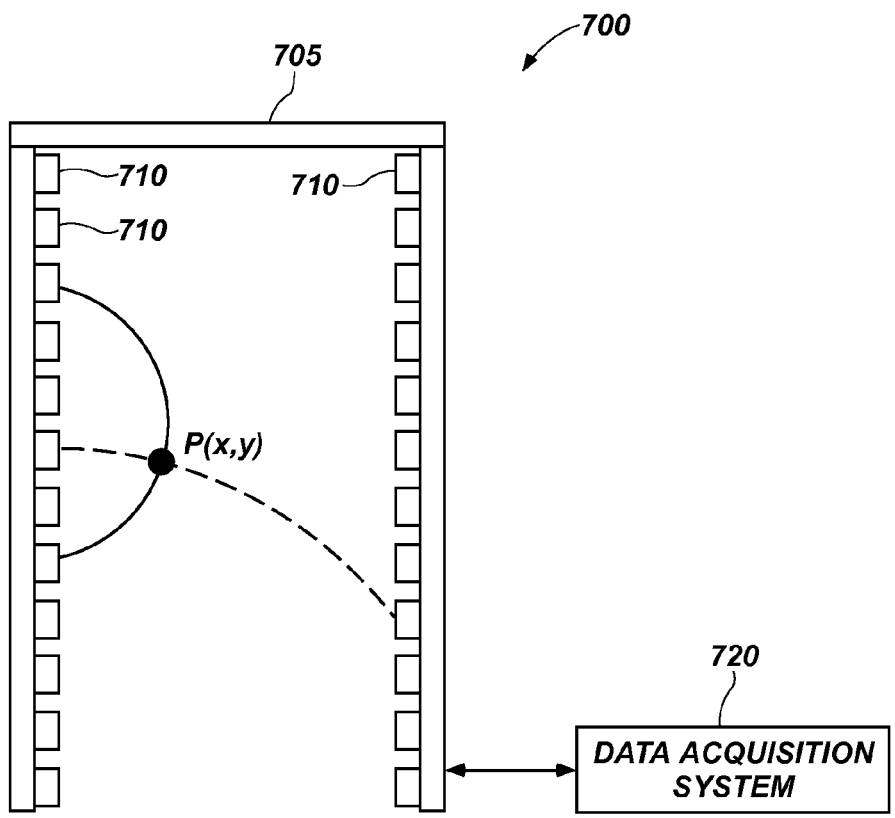
FIG. 7 is a THz imaging system according to another embodiment of the present disclosure.

FIG. 7 is a THz imaging system 700 according to another embodiment of the present disclosure. The THz imaging system 700 may be configured to perform THz imaging as well as threat detection. In particular, the THz imaging system 700 is in a portal configuration, such as may be present for choke point monitoring at locations such as airports and other secured locations. The THz imaging system 700 may include a plurality of discrete sensors 710 disposed about a portal 705 through which a person may pass through. Each discrete sensor 710 may be coupled to a data acquisition system 720 configured to receive the data from the discrete sensors 710 and perform analysis thereof. In particular, the data from each discrete sensor 710 may be concurrently processed for visualization and detection of a threat (e.g., explosive material). Not all of the discrete sensors 710 are labeled for convenience so as not to obscure FIG. 7 with repetitive reference numerals.

Each discrete sensor 710 may include a focal plane array having individual pixels that include resonance elements that are tuned to THz frequencies, as discussed above with respect to FIG. 5. The discrete sensors 710 may further include embedded energy transfer elements configured to convert AC signals generated in response to the THz waves to DC signals transmitted to the data acquisition system 720. Real-time visualization of explosive threats may be implemented in the data acquisition system 720 using computer tomography analysis or other suitable methods. One method may be a derivative of classical x-ray tomography algorithms. For some embodiments, such X-ray algorithms may be computationally intensive and may not be suitable for real-time response.

Instead, a sensitivity zone distribution approach may be implemented to perform tomography where the sensitivity zones approximately follow unperturbed THz induced magnetic flux lines, which may be approximated as curved "rays." A generalized back projection method may be employed to invert the data and to obtain the images of permeability distribution. In some embodiments, the discrete sensors 710 may be deployed in a passive mode. In some embodiments, the discrete sensors 710 may be deployed in an active mode. Each discrete sensor 710 may also be configured to generate a THz wave used as a THz source, while the other discrete sensors may be configured as receivers. For example, a first discrete sensor 710 may operate as a THz source while each of the remaining discrete sensors 710 may read the data from their focal plane arrays. A second discrete sensor 710 may then operate as a THz source while the remaining discrete sensors 710 (including the first discrete sensor 710) may read the data from their focal plane arrays, and so on. By comparing the data from each of the discrete sensors 710, a multidimensional image may be reconstructed. As a result, a location (e.g., P(x,y)) may be identified where a threat object (e.g., explosive material) may be present.

As discussed above, embodiments of the present disclosure may include one or more frequency-selective filters such that THz detection systems are configured to perform single-point absorption peak measurements and matched-filter analysis. As a result, some embodiments may not require a pulsed laser or scanning of the full spectrum and FFT post processing of datasets, as is the case with conventional methods. In addition, relatively simple hardware, with minimal software overhead may be employed. Rather, a small-form factor, embedded controller may be used to implement methods of the present disclosure, which may enable the construction of a handheld tool that is portable and relatively inexpensive, and that may detect explosive materials with a near real-time response.

Figure 8:
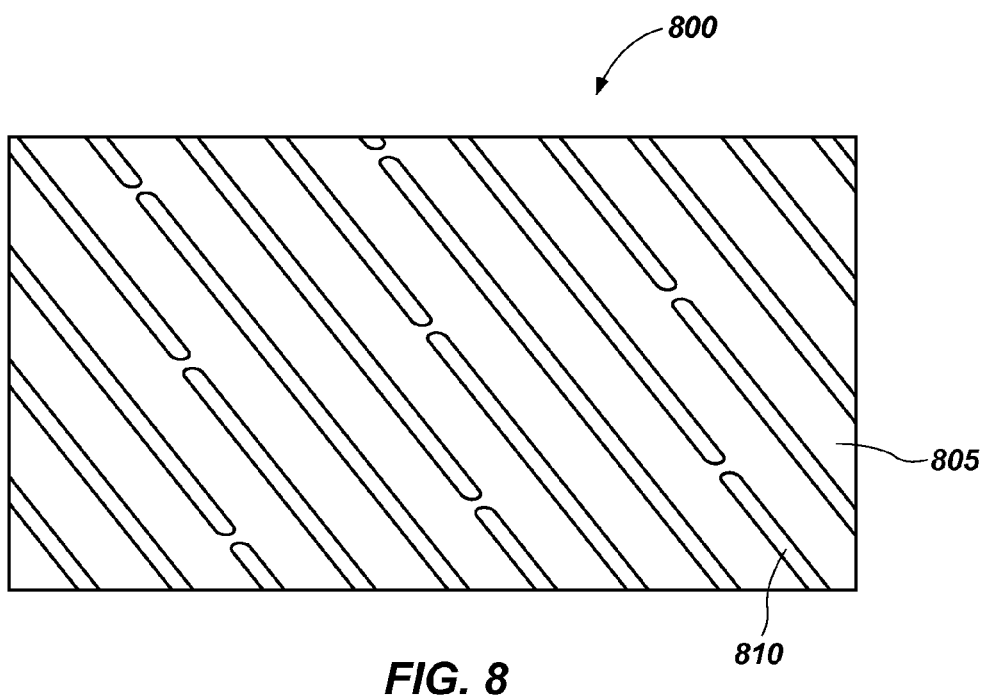
FIG. 8 is a zoomed-in, enlarged view of a portion of a spectral selective filter according to an embodiment of the present disclosure.

FIG. 8 is a zoomed-in, enlarged view of a portion of a spectral selective filter 800 according to an embodiment of the present disclosure. The spectral selective filter 800 may be configured as a front lens to a focal plane array (FIGS. 5-7). For example, the spectral selective filter 800 may be a planar device that is configured to fit well into optical systems.

The spectral selective filter 800 may include resonance elements 810 (e.g., antenna elements) formed on a substrate 805. As a result, the spectral selective filter 800 may include FSS structures that are effectively printed circuits on a substrate. The resonance elements 810 may be configured to have one of a variety of geometries (e.g., dipole, spiral, etc.), such as those described above for the focal plane arrays. The spectral selective filter 800 may be formed with appropriate materials that exhibit optical properties that support THz operation. The resonance elements 810 may be configured as single-layer devices or multi-layer devices. The spectral selective filter 800 may exhibit the electrical behavior of a bandpass filter. The frequency range for the bandpass filter for the resonance elements 810 may be a function of geometry and refractive index of associated thin film materials. The transmission bandpass of the spectral selective filter 800 may be tailored to match the absorption bands of the explosives of interest (e.g., RDX, TNT, etc.).

In some embodiments, the spectral selective filter 800 may be configured as a gangbuster narrow band THz filter. A gangbuster filter may alter the transmission properties of THz energy by controlling the polarization of light from its constituent components (i.e., the time-varying electric and magnetic fields). The polarization of light is defined by the electric field vector in the plane that includes both the electric field vector (E) and the propagation vector (k). If the plane remains stationary as the wave propagates, the polarization is defined as linearly polarized.

The spectral selective filter 800 may include resonance elements 810 that are configured as periodic arrays comprising a gangbuster frequency selective surface. The resonance elements 810 may be configured as relatively straight dipole antenna elements with a length comparable to the wavelength of incident radiation. The dipole antenna elements may be staggered at angles such that there are no grating lobes resulting from periodicity along the length of the elements. The electric field of the incident radiation may be linearly polarized at such an angle that the electric field of the transverse magnetic (TM) mode is along the length of the resonance elements 810. The transverse electric (TE) mode may be reflected.

The spectral selective filter 800 may act as a "matched filter" to provide a spectral selective response to the predefined features of a material of interest. In other words, the resonance elements 810 of the spectral selective filter 800 may be configured to match the filter/detector transmission bandpass to be approximately the absorption band of the material of interest. When implemented in a system configuration, the instantaneous bandwidth of the spectral selective filter 800 may be matched to the instantaneous bandwidth of the source, which may improve sensitivity and reduce inferences. For example, when a THz source is mated to a synchronized detector operating in a virtual "lock-in" mode, the SNR may be improved and standoff detection range will be expanded.

In some embodiments, the spectral selective filter 800 may be formed with the substrate 805 that includes a polyimide material or other suitable material. The spectral selective filter 800 may be fabricated to a thickness that is relatively thin to avoid Fabry-Perot "etalon" fringes (i.e., interference oscillations). The resonance elements 810 (e.g., antenna elements) may be formed on the substrate 805, such as by being embedded in a thin symmetrical substrate (same thickness and material above and below the elements). In some embodiments, the substrate 805 may be a liquid polyimide, and the resonance elements 810 may be formed through an evaporation process, which may provide flexibility in terms of fabrication. For example, silver (Ag) may be selected for the antenna metal because Ag has a relatively low DC resistivity in comparison to other metals in the bulk form. The Ag elements that may be submerged between layers of liquid polyimide are thin relative to the wavelength of the anticipated incident radiation. This fabrication method may prevent unwanted substrate modes that may occur if the filters were fabricated on silicon (Si) wafers. Of course, some methods of the present disclosure may include resonance elements fabricated on a bulk semiconductor material.

Each spectral selective filter 800 may include a single plane of resonance elements 810, which may be sensitive to only one polarization. In some embodiments, the spectral selective filter 800 may be "multi-layer" (i.e., include a plurality of planes of resonance elements 810) formed on each other. Such a multiple-layer configuration may include each plane of resonance elements 810 to be separated by a dielectric to increase the transmission through the structure. Such a dielectric material may include polyethylene, benzocyclobutene (BCB), or other suitable material that may be used to match the impedance of each stack of resonance elements 810 to avoid double interface reflections caused by the impedance mismatches.

For fabrication of a multi-layer spectral selective filter 800, the BCB may be deposited with varying thicknesses, and would adhere to the substrates. BCB can be spun onto a wafer, the thickness can be controlled by the spin speed. For example, BCB may be spun onto a surface at a thickness of 150 nm. BCB may be diluted from its original concentration, such as by using a solvent (e.g., mesitylene). As an example, a ratio of 10 parts BCB to 30 parts mesitylene by weight and spun at a speed of 3000 rpm to achieve the desired thickness of 150 nm as measured on an ellipsometer. In another embodiment, a thickness of 285 nm may be achieved by diluting the BCB to a ratio of 10:15 BCB: mesitylene and spun at a speed of 3000 rpm. Using BCB during fabrication may be desirable for multi-layer configurations because once BCB has been thermally cured, another layer may be spun on without intermixing with the layer beneath. In this way, several layers can be applied and as long as each layer is cured, the total thickness will be the sum of the individual layers.

CONCLUSION

An embodiment of the present disclosure includes a terahertz imaging device. The terahertz imaging device comprises a focal plane array including a substrate and a plurality of resonance elements. The plurality of resonance elements comprise a conductive material coupled to the substrate. Each resonance element of the plurality of resonance elements is configured to resonate and produce an output signal responsive to incident radiation having a frequency between about a 0.1 THz and 4 THz range.

Another embodiment of the present disclosure includes a terahertz imaging system. The terahertz imaging system comprises a focal plane array and a data acquisition system. The focal plane array has a plurality of pixels, each pixel having a resonance element configured to absorb incident radiation, resonate at a frequency in the THz range, and responsively generate an output. The data acquisition system is configured to interpret the output to provide at least one of image data and spectral data.

Yet another embodiment of the present disclosure includes a method of detecting at least one hazardous material. The method comprises receiving incident radiation by a focal plane array having a plurality of discrete pixels including a resonance element configured to absorb the incident radiation at a resonant frequency in the THz, generating an output signal from each of the discrete pixels, and determining a presence of at least one hazardous material by interpreting spectral information from the output signal.

While the present disclosure is susceptible to various modifications and alternative forms, specific embodiments have been shown by way of example in the drawings and have been described in detail herein. However, the disclosure is not intended to be limited to the particular forms disclosed. Rather, the disclosure covers all modifications, combinations, equivalents, and alternatives falling within the scope of the following appended claims and their legal equivalents.

What is claimed is:

1. A terahertz imaging device, comprising:
   a focal plane array including:
      a substrate; and
      a plurality of resonance elements comprising a conductive material coupled to the substrate, wherein:
         each resonance element of the plurality of resonance elements exhibits a resonant frequency in the THz range, and is configured to resonate and produce an output signal responsive to incident radiation at about its resonant frequency;
         the plurality of resonance elements is arranged in a plurality of sub-arrays;
         each sub-array includes resonance elements that are tuned to a different frequency that corresponds to a different spectral absorption peak for at least one material of interest such that resonant elements of a first sub-array are tuned to a first spectral absorption peak for a first material of interest, and resonant elements of a second sub-array are tuned to a second spectral absorption peak of the first material of interest; and
         each resonant element includes an antenna coupled detector that includes a diode for converting incident radiation to DC in a time sufficient for imaging.

2. The terahertz imaging device of claim 1, further comprising a spectral selective filter positioned in a path of the incident radiation prior to the focal plane array, wherein the spectral selective filter includes a plurality of resonance elements tuned to exhibit a resonant frequency for a narrow band THz frequency.

3. The terahertz imaging device of claim 2, further comprising a terahertz radiation source configured to illuminate an object of interest to induce an emission from the object of interest that is received by the focal plane array as the incident radiation.

4. The terahertz imaging device of claim 3, wherein a frequency for a signal generated by the terahertz radiation source and the resonant frequency of the plurality of resonance elements of the spectral selective filter are matched.

5. The terahertz imaging device of claim 3, wherein the terahertz radiation source and the focal plane array are arranged relative to the object of interest to operate the terahertz imaging device in a back scatter mode.

6. The terahertz imaging device of claim 3, wherein the terahertz radiation source and the focal plane array are arranged relative to the object of interest to operate the terahertz imaging device in a reflection mode.

7. The terahertz imaging device of claim 2, wherein the focal plane array is tuned for a broader band than the spectral selective filter.

8. The terahertz imaging device of claim 7, wherein the spectral selective filter is tuned for a narrow band selectivity for absorption lines of a pre-determined chemical specie.

9. The terahertz imaging device of claim 1, wherein resonant elements of a third sub-array are tuned to a third spectral absorption peak for the first material of interest, and resonant elements of a fourth sub-array are tuned to a fourth spectral absorption peak of the first material of interest.

10. The terahertz imaging device of claim 1, further comprising a portal including a plurality of discrete sensors, wherein each discrete sensor of the plurality of discrete sensors includes the focal plane array.

11. The terahertz imaging device of claim 1, wherein resonant elements of a third sub-array are tuned to a first spectral absorption peak for a second material of interest, and resonant elements of a fourth sub-array are tuned to a second spectral absorption peak of the second material of interest.

12. The terahertz imaging device of claim 1, wherein the first material of interest is RDX, the first spectral absorption peak being selected from one of the group consisting of approximately 0.82 THz, 1.05 THz, 1.50 THz, 1.96 THz, 2.2 THz, and 3.08 THz, and the second spectral absorption peak being selected from another of the group consisting of approximately 0.82 THz, 1.05 THz, 1.50 THz, 1.96 THz, 2.2 THz, and 3.08 THz.

13. A terahertz imaging system, comprising:
   a portal having a plurality of discrete sensors, wherein each discrete sensor comprises a focal plane array having a plurality of pixels, each pixel having a resonance element configured to absorb incident radiation, resonate at a frequency in the THz range, and responsively generate an output, wherein the resonance elements are arranged in a plurality of sub-arrays of the focal plane array that are each tuned to a different frequency corresponding to a different spectral absorption peak for at least one material of interest, wherein the portal is configured to operate a first discrete sensor as a THZ source and read data from the focal plane arrays of the other discrete sensors, and then operate a second discrete sensor as a THZ source and read data from the focal plane arrays of the other discrete sensors, and continue operating a different discrete sensor as a THZ source and reading data from the focal plane arrays of the other discrete sensors until each of the plurality of discrete sensors has been operated as a THZ source; and a data acquisition system configured to construct a multidimensional image that can identify the location of a threat object in the portal.

14. The terahertz imaging system of claim 13, wherein the resonance element in each focal plane array has a shape selected from the group consisting of a simple dipole, a bowtie dipole, a spiral, a square loop, a square spiral, a circular loop, concentric loops, an ellipse, a rectangle, a triangle, and a cross.

15. The terahertz imaging system of claim 13, wherein the resonance element in each focal plane array includes an electrically conductive material that is selected from the group consisting of manganese (Mn), gold (Au), silver (Ag), chromium (Cr), copper (Cu), aluminum (Al), platinum (Pt), nickel (Ni), iron (Fe), lead (Pb), tin (Sn), and titanium (Ti).

16. The terahertz imaging system of claim 13, further comprising a spectral selective filter for each focal plane array having a plurality of resonance elements configured to pass a narrow band of the incident radiation to each focal plane array.

17. The terahertz imaging system of claim 16, wherein the spectral selective filter is configured as a gangbuster filter.

18. The terahertz imaging device of claim 13, wherein the resonance elements are selected from the group consisting of antennas, microantennas, nanoantennas, and nanoparticles.

19. A method of detecting at least one hazardous material, the method comprising:
 filtering incident radiation through a spectral selective filter having a first plurality of resonance elements configured to pass a narrow band of the incident radiation;
 receiving the filtered incident radiation by a focal plane array having a plurality of discrete pixels including a second plurality of resonance elements configured to absorb the filtered incident radiation at a resonant frequency in the THz range for a plurality of sub-arrays that are tuned to different frequencies corresponding to different spectral absorption peaks for at least one hazardous material of interest such that resonant elements of a first sub-array are tuned to a first spectral absorption peak for a first material of interest, and resonant elements of a second sub-array are tuned to a second spectral absorption peak of the first material of interest;
 generating an output signal from each of the discrete pixels; and
 determining a presence of at least one hazardous material of interest by interpreting spectral information from the output signal.

20. The method of claim 19, wherein receiving incident radiation by a focal plane array includes passively receiving the incident radiation that was emitted from an object of interest.

21. The method of claim 19, wherein receiving incident radiation by a focal plane array includes actively receiving the incident radiation that was emitted from an object of interest in response to illuminating the object of interest with a terahertz radiation source.

22. The method of claim 19, wherein the hazardous material of interest is selected from the group consisting of chlorine gas, mustard gas, insecticide, sarin gas, cyclosarin, soman, CS gas, tear gas, anthrax bacteria, and botulinum.

23. A terahertz imaging device, comprising:
 a focal plane array including:
  a substrate; and
  a plurality of resonance elements comprising a conductive material coupled to the substrate, wherein:
   each resonance element of the plurality of resonance elements exhibits a resonant frequency in the THz range, and is configured to resonate and produce an output signal responsive to incident radiation at about its resonant frequency;
   the plurality of resonance elements is arranged in a plurality of sub-arrays;
   each sub-array includes resonance elements that are tuned to a different frequency that corresponds to a different spectral absorption peak for at least one material of interest; and
   each resonant element includes an antenna coupled detector that includes a diode for converting incident radiation to DC in a time sufficient for imaging; and
 wherein each resonance element of at least one sub-array includes a bowtie dipole antenna having an inner width of approximately 2.51 µm, an outer width of approximately 42.36 µm, and a port gap width of approximately 2.41 µm.

* * * * *